(12) United States Patent
Klip et al.

(10) Patent No.: US 8,333,725 B2
(45) Date of Patent: Dec. 18, 2012

(54) DEVICE COMPRISING A CONTAINER SYSTEM FOR A BODILY FLUID

(75) Inventors: Evert Jan Klip, Dalen (NL); Carl Gustav Figdor, 's-hertogenbosch (NL)

(73) Assignee: Klip Consultancy B.V., Dalen (NL)

( * ) Notice: Subject to any disclaimer, the term of this patent is extended or adjusted under 35 U.S.C. 154(b) by 790 days.

(21) Appl. No.: 12/306,321

(22) PCT Filed: Jun. 27, 2007

(86) PCT No.: PCT/NL2007/050311
§ 371 (c)(1),
(2), (4) Date: May 13, 2009

(87) PCT Pub. No.: WO2008/002135
PCT Pub. Date: Jan. 3, 2008

(65) Prior Publication Data
US 2009/0286221 A1    Nov. 19, 2009

(30) Foreign Application Priority Data

Jun. 29, 2006    (NL) ..................................... 2000116

(51) Int. Cl.
*A61M 5/00*    (2006.01)
*B01D 21/26*    (2006.01)
(52) U.S. Cl. ............................................. 604/7; 494/37
(58) Field of Classification Search .................. 137/613; 604/7; 494/37
See application file for complete search history.

(56) References Cited

U.S. PATENT DOCUMENTS

| 4,767,397 A | 8/1988 | Hohenberg et al. |
| 4,850,952 A | 7/1989 | Figdor et al. |
| 2002/0142909 A1 | 10/2002 | Sakota |
| 2003/0195104 A1 | 10/2003 | Hlavinka et al. |
| 2006/0122048 A1 | 6/2006 | Hlavinka et al. |

FOREIGN PATENT DOCUMENTS

| DE | 4340678 A1 | 6/1995 |
| EP | 1138392 A2 | 10/2001 |
| JP | 09-108333 | 4/1997 |
| JP | 2001276663 | 10/2001 |
| NL | 1006731 C2 | 2/1999 |

*Primary Examiner* — Maryam Monshipouri
(74) *Attorney, Agent, or Firm* — The Webb Law Firm, PC

(57) ABSTRACT

The invention relates to a device for separating a bodily fluid, in particular blood platelet concentrate, into fractions under centrifugal force. The device comprises a flexible container system which comprises at least a first container for the fluid to be separated and a second container for a separated fraction, wherein the containers are mutually connected using a connecting conduit for a fluid, wherein a widened portion is arranged in the connecting conduit between the first and second container, wherein during use a detectable separating layer is created in the widened portion. The invention also relates to a flexible container system intended for the device, a method for separating blood platelet concentrate into fractions under centrifugal force, and a blood platelet concentrate with low leukocyte content.

10 Claims, 2 Drawing Sheets

DEVICE COMPRISING A CONTAINER SYSTEM FOR A BODILY FLUID

This application is a 371 of PCT/NL2007/050311, filed Jun. 27, 2007, which claims priority to Dutch patent application No. 2000116 filed Jun. 29, 2006.

BACKGROUND OF THE INVENTION

1) Field of the Invention

The invention relates to a device for separating a bodily fluid into fractions under centrifugal force, which device comprises a flexible container system, this container system comprising at least a first container for the fluid to be separated and a second container for a separated fraction, wherein the containers are mutually connected using a connecting conduit for a fluid. The invention also relates to a method for separating blood platelet concentrate into fractions under centrifugal force.

2) Description of the Prior Art

Human blood substantially comprises four components, i.e. blood plasma, blood platelets (thrombocytes), white blood cells (leukocytes) and red blood cells. The white blood cells and the blood platelets are together also referred to as buffy coat, and usually form about 1% of the blood. The red blood cells form about 45% of the blood, while the remaining part, i.e. about 54%, is formed by blood plasma. The demand for the different blood constituents in the purest possible form is considerable and continues to increase. Different methods are known from the prior art for producing blood products by separating the different constituents from each other. A known method for separating whole blood into different fractions such as red cells, blood platelets and plasma comprises of applying centrifugal force. In such a method a plastic container with a unit of whole blood of for instance between 400-550 ml is placed in a centrifuge. By applying centrifugal forces the components of the blood are separated from each other into layers, wherein the layer distribution is determined by the specific weight of the constituents of the blood. The container with the different layers is subsequently removed carefully from the centrifuge and placed in a pressing device with which the layers are pressed to different containers. Using this container system there is the possibility of separating blood during centrifuging thereof into the different blood constituents, wherein different blood constituents enter different containers. Using such a separation technology blood products, i.e. blood constituents, are obtained in a relatively pure form and in a satisfactory yield. The above described method can also be applied directly in the case of a blood donor, wherein blood is taken and then separated. The desired blood products are pressed and collected and the other constituents are returned directly to the donor. This method is known to the skilled person under the name apheresis. In order to increase the quality of the thus obtained blood products to the desired level, they have to be filtered in order to thereby reduce particularly the leukocyte content. Because of better clinical effects, blood products with a reduced content of leukocytes have a higher value, and therefore also a higher price. Particularly blood platelet concentrates obtained in accordance with the above method have too high a leukocyte content. An additional step is necessary in order to make a blood platelet concentrate from whole blood. For this purpose a number of blood platelet concentrates are generally combined and separately centrifuged once again so that at least part of the leukocytes are separated. After centrifuging, the blood platelet concentrate freed of leukocytes is pressed to a separate container via a conduit. After this step the blood platelet concentrate is then filtered once again in order to comply with the current standards for blood products, wherein the limit for low-leukocyte blood components is generally set at a leukocyte content lower than 1 million leukocytes per therapeutic unit. It is however generally known from the literature that contact of blood constituents with filter material of leukocyte filters has an adverse effect on the quality of the relevant blood constituents. Enzymes and cytokines can for instance thus be released from the leukocytes, which is undesirable. Part of the constituents is generally also lost because they remain behind in the filter. Blood platelets in particular are found to be very sensitive to such an additional filtration, among other reasons because of the high activation sensitivity. Other side-effects are described in the literature. In addition to the stated quality aspects of the blood platelets, another factor is that an additional processing step must be performed. The use of leukocyte filters moreover has a cost increasing effect.

NL 1006731 C2 describes a device for separating a bodily fluid into fractions under centrifugal force. The device comprises a flexible container system with containers which are mutually connected using connecting conduits. While a reasonable degree of separation can be achieved with the device described in NL 1006731 C2, this is not however at the desired level.

The present invention has for its object to provide a device and method for separating a bodily fluid, in particular blood platelet concentrate, into fractions under centrifugal force, wherein a high-quality blood product is obtained. The present invention has the particular object of providing a device and method for separating blood platelet concentrate into fractions under centrifugal force wherein a low-leukocyte blood platelet concentrate is obtained.

SUMMARY OF THE INVENTION

A device for separating a bodily fluid into fractions under centrifugal force is provided for this purpose by the present invention which is characterized in that the device comprises a flexible container system, which container system comprises at least a first container for the fluid to be separated, and a second container for a separated fraction, wherein the containers are mutually connected using a connecting conduit for a fluid, wherein a widened portion is arranged in the connecting conduit between the first and second container, wherein during use a detectable separating layer is created in the widened portion. The widened portion provides, among other things, for a better detection of the different separated components and enables a more precise separation and pressing of the components. Although the following explanation must not be deemed as limitative, the inventors believe that the widened portion results in a lower flow speed of the fluid which is pressed or pumped from the outer side of the centrifuge to the inner side under the influence of the applied centrifugal force field. Owing to the lower flow speed the heavier constituents, such as for instance the leukocytes, are kept better separated, or are separated again, from the lighter constituents by the centrifugal force field. By arranging the widened portion in the conduit in the centrifugal force field between the first container (where the first separation takes place) and the second container it becomes possible for instance to prepare platelet concentrates with a remaining leukocyte content of less than 5 million per unit, preferably less than 3 million per unit, most preferably less than 1 million per unit.

It is noted that a device for separating whole blood into fractions under centrifugal force is known from US 2003/

1195104 A1 wherein the containers are mutually connected using connecting conduits in which a widened portion can be arranged. According to US 2003/195104 A1 the widened portion acts as collecting container for buffy coat, and not as a means for obtaining a more precise second separation between bodily fluid components, and in particular between blood platelets and leukocytes, during centrifugation.

The device and method according to the invention are particularly suitable for the preparation of blood platelet concentrates, and particularly those with a reduced leukocyte content.

The widened portion in the conduit system can take diverse forms. It is thus possible for the widened portion to be trapezium-shaped, cylindrical, rectangular or to take any other suitable form. The only limitation set on the form thereof is that it must result in a decrease in the average flow speed of the fluid relative to the average flow speed in the conduit. According to the invention the widened portion is connected to the first container via an incoming conduit and to the second container via an outgoing conduit. When the container system according to the invention is received in a centrifuge, the incoming conduit is preferably positioned at the largest radius of the centrifuge, while the outgoing conduit is preferably positioned at a smaller radius. The widened portion can be both flexible and rigid. The widened portion can thus be manufactured for instance from an injection-moulded plastic, wherein the widened portion is preferably relatively flat. The widened portion is preferably also transparent enough to enable detection of the separating layer, for instance by optical means.

A preferred embodiment of the device according to the invention is characterized in that the device is provided with means using which the connecting conduit between the first container and the widened portion and/or between the widened portion and the second container can be blocked and unblocked. The means with which the connecting conduit between the containers can be blocked and unblocked preferably comprise clamping means. Such clamping means can pinch shut (block) or leave clear (unblock) the connecting conduit between the respective containers depending on the situation desired. It is also possible for the clamping means to be coupled to the centrifuge device, while the device according to the present invention is provided with members, for instance openings, which can co-act with the clamping means and thus contribute toward (un)blocking of the connecting members.

The blocking means in the device can provide for a blocking (closure) or unblocking (opening) of the connecting conduit between the containers. The device can be placed, together with the container system coupled thereto, in a space suitable for the purpose in a centrifuge device. A plurality of devices are preferably processed simultaneously in the centrifuge. Is also possible to process only one device in the centrifuge, for instance when an annular container system is applied as first container. An example of such a centrifuge device is that of the Orbisac® type. If the above described container system is applied in a centrifuge, the blocking means can in the first instance close the connecting conduit between the first container and the widened portion, and the widened portion and the second container, until a separation of blood constituents has taken place in the first container. The connecting conduit between the two containers can then be unblocked so that one of the blood constituent layers can flow out of the first container, via the widened portion, into the second container. According to the invention the widened portion herein provides for a more sharply defined separating layer, and therefore a better separation. When, in the case of a blood platelet concentrate, substantially all the blood platelet-rich plasma has flowed from the first container to the second, the connecting conduit between the first container and the widened portion and between the widened portion and the second container can be closed using one or more blocking means. In order to support the flow from the first container to the second, the device according to the invention comprises pressing means, using which at least the first container can be subjected to a pressure exerted from outside the relevant container. It is also possible to provide the device with a pump device with which the fluid is pumped from the first container to the second container counter to the centrifugal direction.

In a further preferred variant the device comprises detection means for detecting the position of the separated fractions in the widened portion. Use of the widened portion creates a more sharply defined separating layer, the position of which can be detected in simpler and more accurate manner by the detection means. In yet another preferred embodiment the device comprises a row of detection means for detecting the position and the progress of the separated fractions in the widened portion, and in particular of the separating layer. The row of detection means is disposed for this purpose in the direction of flow of the bodily fluid, preferably along the whole or partial length of the widened portion, so that the progress of the separating layer can be followed.

Although in principle any suitable detection means could be applied, it is advantageous if the detection means comprise a light source disposed on one side of the widened portion and a row of light-sensitive sensors which are disposed on the other side of the widened portion and which can measure the intensity of the light scattered by the fluid present in the widened portion. The light-sensitive detectors are preferably set here such that they generate a signal to actuating means present in the device when a determined blood component not to be collected in the second container reaches the outlet conduit of the widened portion. The actuating means then ensure that one or more blocking means are actuated, for instance activated, whereby the conduit to the second container is closed. In order to cause no further mixing once the different separated constituents have been pressed or pumped over, the feed conduits between the first container and the second container are preferably pinched shut and sealed by means of sealing, welding and so forth, prior to stopping of the centrifuge. This can also be done manually once the centrifuge has come to a stop, wherein the clamps remain closed.

Although the device according to the invention operates very well when it comprises two containers, it can be advantageous to characterize the device in that it comprises a container system with more containers, and wherein at least one widened portion is arranged in the connecting conduit between at least two of the containers. An even more precise separation of the blood into its constituents is achieved with such a device.

In a further preferred embodiment the device comprises one or more receiving parts for accommodating a container and/or widened portion, which parts are adapted such that a container and/or a widened portion can be releasably coupled thereto. This preferred variant has the advantage that, by means of the receiving parts with the container system accommodated therein, the device can be easily removed from the centrifuge once the centrifuging operation has ended. A significant advantage hereof is that, because the different blood constituents are situated in the different containers and the passage between these containers is closed using the blocking means, no mixing of the different blood constituents can take place and very pure blood products are obtained. Another important advantage of the device according to the present invention is that it can already be coupled to a container system while one or more other like devices with container systems coupled thereto are placed in a centrifuge and are being subjected to a centrifuging process. When the centrifuging operation has been ended, the devices with the container systems coupled thereto can be exchanged easily and quickly without additional operations having to be performed for the purpose of placing the container system. The use of the present preferred variant therefore greatly enhances the efficiency of the centrifuging operation using the above mentioned container system.

At least one of the receiving parts is preferably embodied such that a container releasably coupled thereto can be subjected to a pressure exerted from outside the container. Such an embodiment of at least one of the receiving parts is important so that pressing of the blood constituents can take place from the first container to the widened portion and/or second container. This pressing is for instance brought about using a pressure cushion which is filled with pressurizing liquid or gas and presses against the container. In order to enable such a pressure cushion—or other pressure means—to press against the container, the pressure cushion preferably lies with at least one side against a wall part of the receiving part. It is also possible to pump the blood constituents.

BRIEF DESCRIPTION OF THE DRAWINGS

The present invention will be further elucidated hereinbelow with reference to the accompanying figures. The figures are purely schematic and not necessarily drawn to scale. Some dimensions are exaggerated for the sake of clarity. In the figures.

DETAILED DESCRIPTION OF THE PREFERRED EMBODIMENTS

Figure 1:
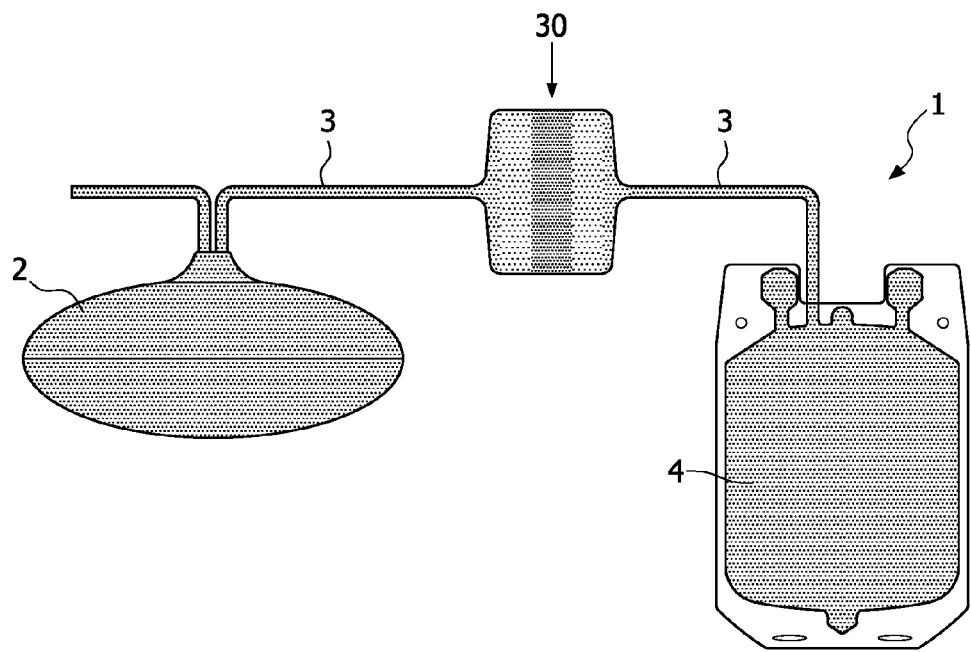
FIG. 1 shows schematically a flexible container system according to the invention suitable for application in the separation of bodily fluids.

FIG. 1 shows an embodiment of a flexible container system 1 for separating bodily fluids, for instance blood and in particular blood platelet concentrate, by means of centrifugation. In the shown embodiment variant the container system 1 comprises a first container 2 and a second container 4. The content of containers 2, 4 is in mutual connection using a hose or tube-like connecting conduit 3. A widened portion 30 is incorporated according to the invention in connecting conduit 3 between first 2 and second container 4. If desired, a plurality of connecting conduits can also be applied. Containers 2, 4, widened portion 30 in connecting conduit 3 as well as connecting conduit 3 itself are preferably formed from a flexible material, generally a transparent plastic. During use of container system 1 a blood platelet concentrate, which is obtained in known manner by separating drawn blood into its constituents, is received in first container 2, after which container system 1 is placed in a centrifuge device, for instance of the Rotomat® type, and the blood platelet concentrate is separated into individual components under the influence of the occurring centrifugal force. If desired, a mixture of multiple buffy coats, for instance 4 to 6, can also be received in first container 2.

Figure 2:
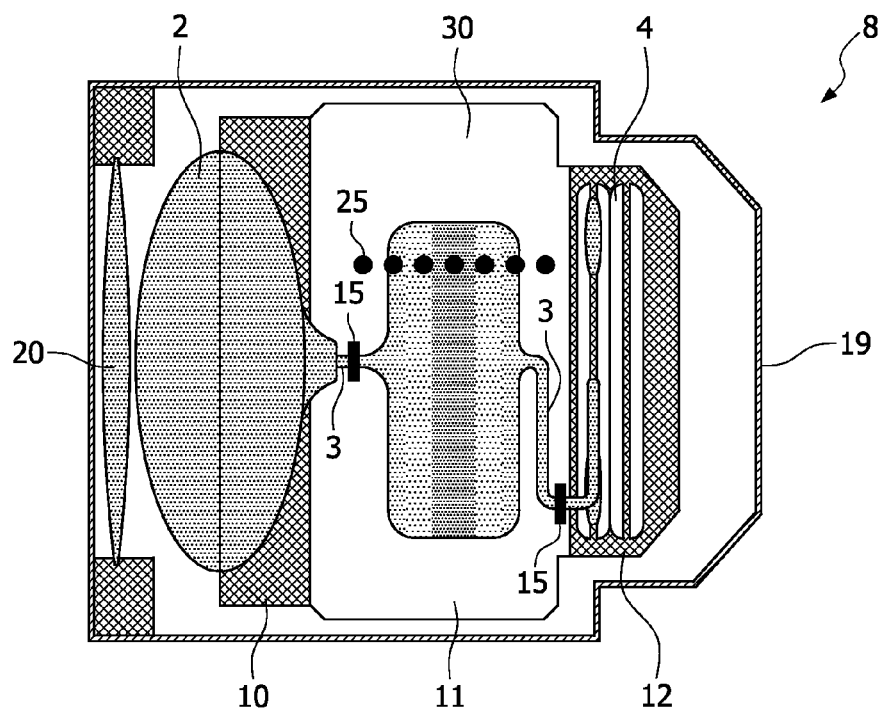
FIG. 2 shows schematically a top view of a device according to the present invention.

During centrifugation of these pooled buffy coats the blood platelet concentrate is separated into a white-yellowish layer of platelets and white blood cells, and into a yellow top layer of plasma and platelets. Once separation of the components has occurred, the top layer of plasma and blood platelets, this being the layer situated closest to the outlet of container 2 after centrifugation, is pressed via widened portion 30 to second container 4. This pressing can take place by exerting a pressure on first container 2 with pressing means 20 using pressurizing liquid or gas, and is preferably performed at a lower rotation speed of the centrifuge. According to the invention the plasma with a relatively high platelet concentration is thus the first to be collected in second container 4. At the moment the white-yellowish layer reaches widened portion 30 in conduit 3 the heavier leukocytes present in the white-yellowish layer are slowed down more by the centrifugal force than the platelets in the plasma. A more precise separating layer is hereby created in widened portion 30. In a preferred embodiment of the invention the device is further provided with clamping means 15 with which the connecting conduit 3 between containers 2, 4 can be blocked and/or unblocked as shown in FIG. 2. In the shown preferred variant the device comprises clamps 15 between first container 2 and widened portion 30, and between widened portion 30 and second container 4. The device further comprises detection means 25 for detecting the position of the separated fractions in widened portion 30, and more specifically of the separating layer between the leukocyte fraction and the plasma fraction, which can otherwise both comprise platelets. In addition to the separation in the first container, an additional second, more precise separation takes place according to the invention due to the use of the widened portion therein. Detection means comprise more precisely a light source disposed on one side (the front side or the rear side of the plane of FIG. 2) of widened portion 30, and a row of light-sensitive sensors which are disposed on the other side of widened portion 30 and which can measure the intensity of the light scattered by the fluid present in widened portion 30. The progress of the separating layer can be measured by disposing the row of sensors in the flow direction of the blood platelet concentrate, preferably along the whole length of the widened portion. This for instance allows precise adjustment of the rotation speed of the centrifuge subject to the measured position of the separating layer. It is thus possible for instance to decrease the rotation speed in stepwise manner the closer the separating layer moves to the outer end on the side of the second container. The specific densities of blood components differ very little. The red blood cells thus have a density of 1.10 g/ml, white blood cells a density of 1.07 g/ml, platelets a density of 1.05 g/ml and plasma a density of 1.03 g/ml. Owing to the very small differences in density between platelets and leukocytes in particular, white cells which bubble upward during pumping/pressing and white cells which are still stuck between the platelets will still be moved in the direction of the outer side of the centrifuge during the second separating step, at a lower rotation speed than in the first separating step. Because the differences in density are so small, it is highly advantageous to be able to control the rotation speed precisely.

The clamp 15 is set into operation depending on the adjustment of the array of light-sensitive sensors 25, whereby the hose conduit 3 between widened portion 30 and collecting container 4 is closed and optionally sealed when the white-yellowish layer has neared the end of widened portion 30. Once centrifuge 21 has been stopped, collecting container 4 can be removed (after sealing of conduit 3) as well as first container 2 and widened portion 30. Depending on the type of centrifugal separating device 21, the above described can be carried out as a single operation or a multiple simultaneous operation. The first and second containers 2, 4 can take diverse forms in accordance with the type of device that is applied. It is thus possible to apply containers with a form that is usual in the technical field, fillable via top and/or bottom, relatively flat and round, provided with a side opening, and so forth. It is also possible according to the invention to perform the method with a single buffy coat or unit of blood platelet-rich plasma.

Figure 3:
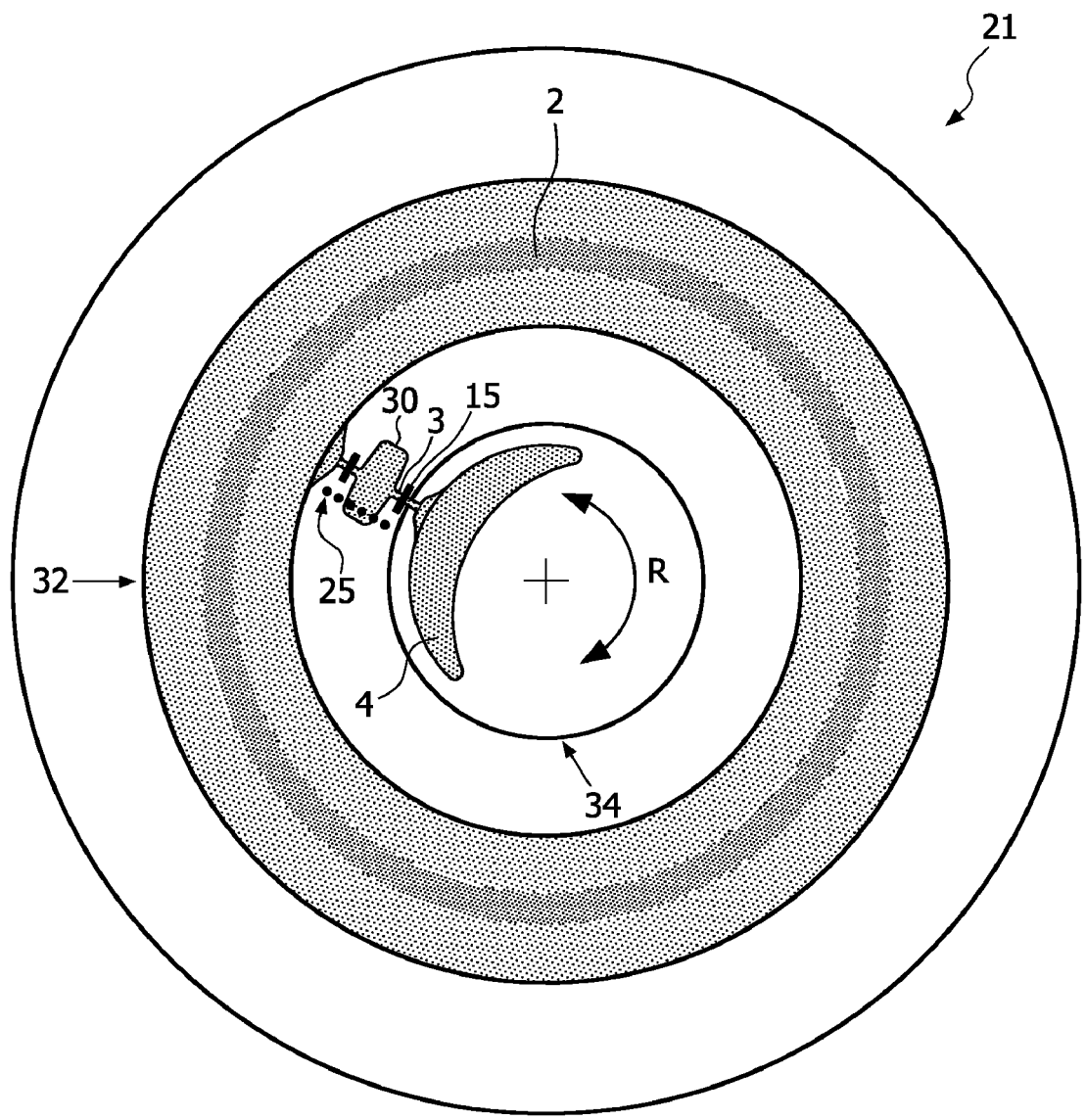
FIG. 3 shows schematically a top view of another embodiment of a device according to the present invention placed in a centrifuge device.

FIG. 2 shows schematically a top view of a part of a device according to the present invention. The shown device is suitable for accommodating a container system 1 according to FIG. 1 and is intended for placing in a centrifuge device 21 as shown in FIG. 3. The device part 8 shown in FIG. 2 comprises three mutually coupled receiving parts 10, 11 and 12, parts 10 and 12 of which are intended for accommodating a container 2, 4 and part 11 of which is intended for accommodating conduit 3 provided with widened portion 30. All components 2, 4, 30 can be coupled releasably to receiving parts 10, 11 and 12. In the shown embodiment receiving part 10 is adapted to accommodate first container 2 of container system 1. Receiving part 10 comprises a space substantially open on one side through which first container 2 can be placed in receiving part 10 and can be coupled thereto, optionally with the use of coupling means. Receiving part 11 is embodied in the shown exemplary embodiment such that conduits 3 and widened portion 30 can be accommodated therein. This receiving part 11 comprises a substantially flat element provided with recesses, among others in the form of widened portion 30, to enable optional easy placing and fixing thereof. If desired, the recess for widened portion 30 can be provided with a cover (not shown) in order to couple widened portion 30 releasably to receiving part 11. Finally, receiving part 12 is intended to accommodate second container 4. This receiving part 12 comprises a hollow space which can optionally be closed using hinged flaps (not shown). Second container 4 can herein be placed in the space, after which it is closed using the flaps. The device part 8 further comprises means 15, using which the connecting conduit 3 between containers 2 and 4 can be blocked and unblocked. These means 15 can comprise openings which co-act with blocking means coupled to the centrifuge device. Another option however is that these means 15 themselves comprise blocking means in the form of clamping means and/or welding devices.

Finally, FIG. 3 shows another preferred embodiment of the device according to the present invention placed in a centrifuge device 21. The shown part of centrifuge device 21 comprises a recess or cavity 32 in which a relatively flat, annular container 2 can be accommodated. FIG. 3 shows container 2 in top view. Centrifuge device 21 is further provided with a pressing member (not shown) which can expand when liquid or gas is supplied and can exert a pressure on first container 2 so that it is—largely—emptied due to the pressing. The pressing member can be situated in the cover or on the bottom of the recess of the centrifuge device and extends over practically the whole surface area of container 2. Centrifuge device 21 is further provided with a second recess 34 in which a second container 4 can be accommodated. Both containers are mutually connected via connecting conduit 3. Connecting conduit 3 is provided according to the invention with a widened portion 30. Light-sensitive sensors 25 can likewise be accommodated in device 21. Centrifuge device 21 is driven by a motor which enables the rotation in the directions R indicated in FIG. 3. The operation of the device according to the present invention, in combination with container system 1, is as follows. As according to the above description, containers 2, 4 and connecting conduit 3 with widened portion 30 are accommodated in the device and coupled releasably thereto. Only container 2 is here filled with blood platelet concentrate. After placing in centrifuge device 21, the centrifuge device is set into operation. In this situation blocking means 15 are activated such that a blocking of connecting conduit 3 takes place so that the concentrate cannot flow from first container 2 to second container 4. In a preferred embodiment blocking means 15 comprise clamping means and/or welding means which can be in the device itself as well as coupled to the centrifuge device. In the shown embodiment clamping means 15 are present on the device itself. The device moreover co-acts with detection and actuating means which are usually coupled to the centrifuge device and can actuate blocking means 15. In the starting situation the detection and actuating means are adjusted such that connecting conduit 3 is blocked. After a determined centrifugation period in which separation of the blood platelet concentrate into the separate components has taken place, blocking means 15 are actuated so that they unblock connecting conduit 3 and a flow of fluid can take place from first container 2 to widened portion 30 and second container 4. This latter is furthermore stimulated by the pressing member which expands by means of supplied liquid or gas and exerts a pressure on first container 2. According to the invention the plasma with a relatively high platelet concentration is thus the first to be collected in second container 4. Incorporating the widened portion 30 into conduit 3 according to the invention is now found to bring about a relatively well-defined separation between the components of the white-yellowish layer of platelets and white blood cells, therefore between platelets and leukocytes. At the moment the white-yellowish layer reaches the widened portion 30 in conduit 3, the heavier leukocytes present in the white-yellowish layer are slowed down more according to the invention by the centrifugal force than the platelets in the plasma. This creates a more precise separating layer in widened portion 30 which can be detected relatively easily by detection means 25. When detection means 25 detect such a change, the actuating means ensure that the blocking means 15 co-acting therewith between widened portion 30 and second container 4 are activated so that the relevant part of connecting conduit 3 is closed and the fluid flow is stopped. The centrifugation process can now be ended and the device can be taken out of centrifuge 21. Due to the invention a blood platelet concentrate will be situated in second container 4 with a lower leukocyte content than has been usual heretofore. It is thus possible to obtain a blood platelet concentrate with a leukocyte content which is lower than 5 million per unit, preferably lower than 3 million per unit, most preferably lower than 1 million per unit. A unit is the usual term used by the skilled person for a therapeutic unit. This has great advantages because it is now no longer necessary to filter the blood platelet concentrate obtained by means of centrifugation in order to thus bring the leukocyte content to the desired low level. Filtering is undesirable because of the negative effects on at least a part of the constituents of the blood platelet concentrate.

The invention claimed is:

1. A device for separating a bodily fluid into fractions under centrifugal force, which device comprises a centrifuge and a flexible container system, the container system comprising at least a first container for the fluid to be separated and a second container for a separated fraction, wherein the containers are mutually connected using a connecting conduit for a fluid, wherein a widened portion is arranged in the connecting conduit between the first and second container, and wherein during centrifugation a detectable separating layer is created in the widened portion, the device further comprising an array of detection means arranged in the direction of flow of the bodily fluid along the whole or partial length direction of the widened portion for detecting the position and the progress of the separated fractions in the widened portion, and in particular of the separating layer.

2. The device as claimed in claim 1, wherein the device further comprises means allowing precise adjustment of the rotation speed of the centrifuge subject to the measured position of the separated layer.

3. The device as claimed in claim 1, wherein the detection means comprise a light source disposed on one side of the widened portion and a row of light-sensitive sensors which are disposed on the other side of the widened portion and which can measure the intensity of the light scattered by the fluid present in the widened portion.

4. The device as claimed in claim 3, wherein the row of light-sensitive sensors is disposed in the direction of flow of the bodily fluid.

5. The device as claimed in claim 1, wherein the device is provided with means using which the connecting conduit between the first container and the widened portion and/or between the widened portion and the second container can be blocked or unblocked.

6. The device as claimed in claim 5, wherein the means with which the connecting conduit between the containers can be blocked and unblocked comprise clamping means and/or welding means.

7. The device as claimed in claim 1, wherein the device comprises actuating means, this such that one or more blocking means are actuated by the actuating means in response to a signal generated by the detection means.

8. The device as claimed in claim 1, wherein the device comprises a container system comprising a plurality of containers, and wherein at least one widened portion is arranged in the connecting conduit between at least two of the containers.

9. The device as claimed in claim 1, wherein the device comprises pressing means or pumping means, using which at least the first container can be subjected to a pressure exerted from outside said container.

10. The device as claimed in claim 1, wherein the device comprises one or more receiving parts for accommodating a container and/or widened portion, which parts are adapted such that a container and/or a widened portion can be releasably coupled thereto.

* * * * *